United States Patent [19]

Kuntz

[11] E Patent Number: Re. 31,812

[45] Reissued Date of Patent: Jan. 22, 1985

[54] CATALYTIC HYDROFORMYLATION OF OLEFINS

[75] Inventor: Emile Kuntz, Lyons, France

[73] Assignee: Rhone-Poulenc Industries, Paris, France

[21] Appl. No.: 393,439

[22] Filed: Jun. 29, 1982

Related U.S. Patent Documents

Reissue of:

[64] Patent No.: 4,248,802
Issued: Feb. 3, 1981
Appl. No.: 696,909
Filed: Jun. 17, 1976

[30] Foreign Application Priority Data

Jun. 20, 1975 [FR] France ..... 75 19407
Apr. 29, 1976 [FR] France ..... 76 12672

[51] Int. Cl.[3] ..... C07C 45/50

[52] U.S. Cl. ..... 568/454; 568/909; 260/428 R; 502/164; 502/166; 502/165

[58] Field of Search ..... 568/454, 455, 909; 252/431 P; 260/429 R

[56] References Cited

U.S. PATENT DOCUMENTS

| | | | |
|---|---|---|---|
| 3,959,385 | 5/1976 | Neinberg | 568/454 |
| 3,976,703 | 8/1976 | Wilkis | 568/454 |
| 4,248,802 | 2/1981 | Kuntz | 568/454 |

FOREIGN PATENT DOCUMENTS

| | | | |
|---|---|---|---|
| 2069332 | 10/1971 | France | 568/454 |

OTHER PUBLICATIONS

Schindbauer, "Monltsch. Chem." vol. 96 (1965) pp. 2051-2057.

*Primary Examiner*—Werren B. Lone
*Attorney, Agent, or Firm*—Burns, Doane, Swecker & Mathis

[57] ABSTRACT

Olefins are hydroformylated to aldehydes in the presence of a catalytic system comprising a rhodium containing, aqueous solution of certain sulfonated aryl phosphine compounds.

37 Claims, No Drawings

CATALYTIC HYDROFORMYLATION OF OLEFINS

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a process for the preparation of aldehydes by hydroformylation of olefins, and, more especially, relates to such hydroformylation of olefins in the presence of a rhodium containing, aqueous solution of certain sulfonated aryl phosphine compounds.

2. Description of the Prior Art

It is well known in the art to produce aldehydes by hydroformylation, by reacting an olefin with carbon monoxide and hydrogen, said process being carried out in an organic liquid medium which contains, as catalyst, a compound based on a metal of Group VIII of the periodic classification or table of elements [compare Handbook of Chemistry and Physis, 53rd edition], and especially which contains a soluble complex formed from one of the above metal compounds and at least one organic ligand which has, in its molecule, an atom of an element of Group VA of the periodic classification, such as tertiary arsines, tertiary stibines or tertiary phosphines.

Among the catalyst systems to date envisaged, those complexes resulting from the reaction of an inorganic or organic derivative of rhodium with an excess of tertiary phosphine, tertiary arsine or tertiary stibine, such as triphenylphosphine, triphenylarsine or triphenylstibine, appear the most attractive. In general, these reactions are carried out in a solvent such as an aromatic hydrocarbon [benzene or toluene], a saturated cycloaliphatic hydrocarbon [cyclopentane or cyclohexane], an ether [diisopropyl ether, dibutyl ether of ethylene glycol], a ketone [acetone or methylethyl ketone], an aliphatic or cycloaliphatic alcohol [methanol, ethanol, butanol, hexanol or cyclohexanol], an ester such as those derived from alkylcarboxylic or arylcarboxylic acids and aliphatic or cycloaliphatic alcohols [ethyl acetate, cyclohexyl acetate, diethyl oxalate or methyl benzoate], or lactones [butyrolactone or valerolactone] [compare, in particular, U.S. Pat. Nos. 3,511,880 and 3,801,646 and French Pat. No. 1,560,961].

Under these conditions, resorting to these complexes based on rhodium and a ligand containing trivalent phosphorus, arsenic or antimony atoms renders it possible to conduct the hydroformylation with very small amounts of noble metal, and at a low pressure. It should further be noted that the concomitant hydrogenation of the aldehydes is extremely slight and that, consequently, the desired aldehydes are the principal products. The hydrogenation of the reactant olefin is also very slight. In the majority of cases, use of these catalyst systems makes it possible to direct the hydroformylation of linear olefins, having a terminal or internal double bond, towards the predominant formation of aldehydes having a linear chain or a short side chain, so that the selectivity of the reaction in this respect, measured by the percentage of linear isomers or of isomers having a short side chain, contained in the aldehyde resultant products, is generally greater than 50%. Thus, this selectivity can be as much as 90%, and even in excess of this value. In the case of the lower linear olefins, such as propylene, it is however to be noted that the achievement of high selectivities in respect of aldehydes having a linear chain requires considerable expenditure on ligands based on phosphorus [triphenylphosphine], on arsenic [triphenylarsine] or on antimony [triphenylstibine], because under these conditions such ligands are themselves used as the reaction medium, in the absence of any other organic solvent [compare French Pat. No. 2,072,146 and British Pat. No. 1,357,735].

Ultimately, the striking catalytic properties of the aforementioned soluble complexes based on rhodium have enriched the state of the art by providing an easily performed method for the preparation of aldehydes. However, a notable disadvantage of those liquid phase hydroformylation processes above described, in which the catalyst systems employed are homogeneous and in solution, resides in the fact that they require a difficult supplementary treatment for the purpose of separating the hydroformylation products from the catalyst solution, and the catalyst is only difficultly recovered in order to recycle same to the reaction zone; for example, the catalyst can be recycled in the non-volatile residue obtained after distillation of the oxygen-containing reaction products. In fact, such a treatment of the catalyst solution can only be validly applied to processes for the hydroformylation of lower olefins which provide volatile reaction products. Furthermore, it has also been found that this treatment gives rise to substantial loss of catalyst; the catalyst solutions decompose readily during the treatment stages so that the noble metal is lost by precipitation of its metallic form. The presence of catalyst in the reaction products after they have been separated is also observed. The residual catalyst system thus loses its efficiency, which reduces the industrial value of such hydroformylation processes.

In order to overcome these disadvantages and reduce the losses of rhodium, it has also been proposed to use a heterogeneous solid catalyst which can easily be separated from the reaction medium, for example, by fixing the rhodium complex on a porous solid support [compare French Pat. No. 2,069,322] or by combining a rhodium derivative with a polymer [polystyrene or polyvinyl chloride] containing a phosphine [compare French Pat. No. 2,047,476]. However, the solid phase catalysts possess certain disadvantages, and, in particular, there has been observed a limitation on the selectivity of the catalyst system with regard to the formation of aldehydes having a linear chain or a short side chain, from linear olefins having a terminal or internal double bond.

A need thus exists to provide a process for the hydroformylation of olefins, in liquid phase, in the presence of a catalyst based on rhodium, which obviates the disadvantages of the prior processes relating to the recovery of the catalyst, while at the same time preserving the aforementioned advantages, especially the high yields of aldehyde products and the excellent selectivities in respect of aldehydes having a linear chain or a short side chain.

SUMMARY OF THE INVENTION

Accordingly, it is a primary object of the present invention to provide an improved process for the hydroformylation of olefins which avoids those difficulties attendant the state of the art.

Yet another object of this invention is to provide an improved process whereby the olefins are catalytically hydroformylated, the catalyst maintaining its efficacy and selectivity throughout the course of the reaction.

Briefly summarized, the present invention relates to a process for the hydroformylation of aliphatic olefins, in liquid phase, to form corresponding aldehyde compounds, which process comprises reacting the olefin with carbon monoxide and hydrogen, characterized in that the reaction is carried out in the presence of an aqueous solution of at least one phosphine having the following structural formula:

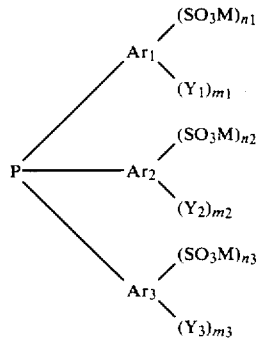

(I)

in which:

$Ar_1$, $Ar_2$ and $Ar_3$, which can be identical or different, represent aryl groups, such as phenyl or naphthyl, the various substituents $Y_1$, $Y_2$ and $Y_3$, which can be identical or different, each represent a linear or branched chain alkyl radical having from 1 to 4 carbon atoms, such as, for example, a methyl, ethyl, propyl, isopropyl or butyl radical, an alkoxy radical containing from 1 to 4 carbon atoms, such as, for example, a methoxy, ethoxy, propoxy or butoxy radical, a halogen atom [chlorine or bromine], a functional group such as a hydroxyl group, a nitrile group, a nitro group or a disubstituted amino group of the formula $NR_1R_2$, in which the radicals $R_1$ and $R_2$, which also may be identical or different, each represent a linear or branched chain alkyl radical having from 1 to 4 carbon atoms, such as a methyl, ethyl, propyl or butyl radical, M is a cationic radical of inorganic or organic origin, selected so that the compound of the formula (I) is water-soluble, $m_1$, $m_2$ and $m_3$ are integers which can be identical or different and range from 0 to 5, and $n_1$, $n_2$ and $n_3$ are integers which can be identical or different and range from 0 to 3, at least one of the chambers $n_1$, $n_2$ or $n_3$ being greater than or equal to 1, the said aqueous solution of the above sulfonated phosphine containing either metallic rhodium or a rhodium containing compound.

By "olefin" there is intended any organic monomer containing at least one carbon-to-carbon double bond; similarly, the dienes and ethylenic compounds containing another functional group can be treated in accordance with the process of the invention.

DETAILED DESCRIPTION OF THE INVENTION

More specifically, this invention relates to the hydroformylation of monoethylenically unsaturated compounds having from 2 to 20 carbon atoms, comprising linear or branched chain olefins having a terminal or internal double bond. By way of non-limiting examples, there are mentioned the ethylenic hydrocarbons such as ethylene, propylene, 1-butene, 2-methyl-1-butene, 2-butene, 1-pentene, 2-pentene, 1-hexene, 3-ethyl-1-hexene, 2-propyl-1-hexene, 2-hexene, 1-heptene, 1-octene, 3-octene, 4,4-dimethyl-1-nonene, 1-decene, 2-decene, 6-propyl-1-decene, 3-udecene, 1-dodecene, 5-tetradecene, 1-octadecene and 2-octadecene.

The hydroformylation process according to the present invention is most suitably applied to the linear aliphatic monoethlenic compounds containing from 2 to 8 carbon atoms, such as ethylene, propylene, 1-butene, 1-pentene, 1-hexene, 2-hexene, 1-heptene and 1-octene.

As phosphines of the formula (I) which are suitable for carrying out the process according to the invention, there are mentioned those in which the cationic radicals M, associated with the sulfonate groups borne by the aromatic rings, are inorganic cations derived from alkali metals or alkaline earth metals such as sodium, potassium, calcium or barium, or derived from metals selected from the group consisting of lead, zinc and copper; further, the cations may be ammonium ions $NH_4^{30}$, in which the radicals $R_3$, $R_4$, $R_5$ and $R_6$, which can be identical or different, each represent a linear or branched chain alkyl radical containing from 1 to 4 carbon atoms, such as methyl, ethyl, propyl or butyl radical.

Among the quaternary ammonium cations, there may be mentioned as preferred the tetramethylammonium, tetraethylammonium, methyltriethylammonium, tetrapropylammonium, triethylbutylammonium and tetrabutylammonium ions.

The preferred phosphines of the formula (I) for carrying out the hydroformylation process according to the invention are those in which:

$Ar_1$, $Ar_2$ and $Ar_3$ are phenyl groups, $Y_1$, $Y_2$ and $Y_3$ represent an alkyl radical such as methyl and ethyl, an alkoxy radical such as methoxy and ethoxy, or a chlorine atom, the cationic radicals M represent inorganic cations derived from metals such as sodium, potassium, calcium and barium, ammonium ions $NH_4+$, or quaternary ammonium ions such as tetramethylammonium ions, and $m_1$, $m_2$ and $m_3$ are integers which may be identical or different and range from 0 to 3.

Most preferably, according to the invention, at least one phosphine is employed corresponding to the formula (1) above, in which $Ar_1$, $Ar_2$ and $Ar_3$ are a phenyl group, $m_1$, $m_2$ and $m_3$ are equal to 0, and $n_1$, $n_2$ and $n_3$ are equal to 0 or 1, $n_1+n_2+n_3$ being between 1 and 3, and the $SO_3H$ groups are in the meta-position.

And of these latter compounds, the phosphines corresponding to the following formulae are preferred:

(II)

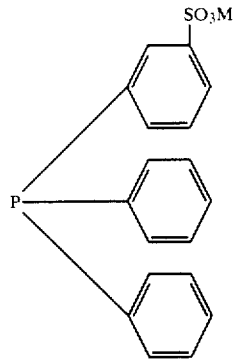

(III)

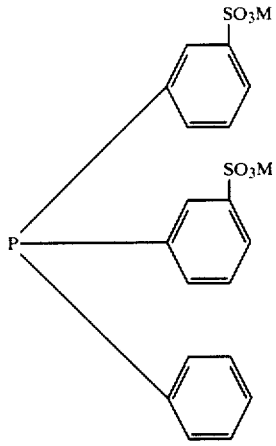

and (IV)

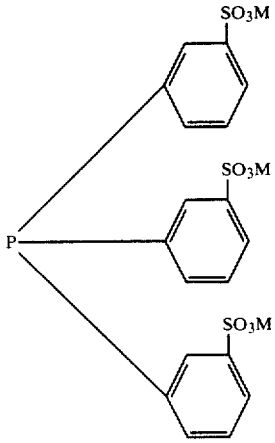

According to yet another most preferred embodiment of the process according to the invention, a mixture of at least two of the phosphines corresponding to the formulae II, III and IV is employed.

By way of non-limiting examples of compounds of the formula (I) which are suitable for the present invention, there may furthermore be mentioned the alkali metal salts or alkaline earth metal salts, the ammonium salts and the quaternary ammonium salts of (p-sulfophenyl)diphenylphosphine, (m-sulfo-p-methylphenyl)-di(p-methylphenyl)phosphine, (m-sulfo-p-methoxyphenyl)di(p-methoxyphenyl)phosphine, (m-sulfo-p-chlorophenyl)di(p-chlorophenyl)phosphine,di(p-sulfophenyl)phenylphosphine, di(m-sulfo-p-methylphenyl)(p-methylphenyl)phosphine, di(m-sulfo-p-methoxyphenyl) (p-methylphenyl)phosphine, di(m-sulfo-p-chlorophenyl) (p-chlorophenyl)phosphine, tri(p-sulfophenyl)phosphine, tri(m-sulfo-p-methylphenyl)-phosphine, tri(m-sulfo-p-methoxyphenyl)phosphine, tri(m-sulfo-p-chlorophenyl)phosphine, (o-sulfo-p-methylphenyl) (m-sulfo-p-methyl) (m,m'-disulfo-p-methyl)phosphine and (m-sulfophenyl) (m-sulfo-p-chlorophenyl) (m,m'-disulfo-p-chlorophenyl)phosphine.

The sodium, potassium, calcium, barium, ammonium, tetramethylammonium and tetraethylammonium salts of (sulfophenyl)diphenylphosphine, di(sulfophenyl)-phenylphosphine and tri(sulfophenyl)phosphine are particularly suitable for conducting the subject process.

The sulfonated phosphines of the present invention can be prepared according to known processes. Thus, according to the teaching of H. Schindbauer, Monatsch. Chem., 96, pages 2051–2057 (1965), the sodium salt of (p-sulfophenyl)diphenylphosphine can be prepared by reacting sodium p-chlorobenzenesulfonate with diphenylchlorophosphine in the presence of sodium or of potassium. According to the method described in J. Chem. Soc., pages 276–288 (1958) and in British Pat. No. 1,066,261, phenylphosphines of the formula (I) can be prepared by employing the reaction wherein aromatic nuclei are sulfonated by means of oleum, and then neutralizing the sulfonic acid groups formed, by means of a suitable basic derivative of one of the metals which M represents in the formula (I). The crude sulfonated phosphine obtained can contain, as an admixture, the corresponding oxide of the sulfonated phosphine, the presence of which, however, does not interfere with the execution of the hydroformylation process according to the present invention.

As regards the rhodium used to carry out the process of the invention, this can be metallic rhodium, preferably deposited on various supports such as carbon black, calcium carbonate, aluminas or equivalent materials.

As the rhodium containing compound, compounds which are water-soluble or capable of going into aqueous solution under the reaction conditions are employed. The radical linked to the rhodium is not critical as long as it satisfies these conditions. Among these compounds, there are mentioned, by way of illustration, the following inorganic or organic derivatives of rhodium, in which the rhodium atom can be at various oxidation levels: the rhodium oxides, the salts of inorganic hydracids such as rhodium chloride, bromide, iodide, sulfide, selenide and telluride, the salts of inorganic oxyacids as rhodium sulfite, sulfate, nitrate, perchlorate or selenate, and the salts of aliphatic monocarboxylic acids such as rhodium acetate, propionate, oxalate and malonate.

Other suitable inorganic or organic salt-like compounds falling within the scope of the invention are the salts of heteropolyacids containing rhodium, such as the salts of alkali metals or alkaline earth metals, ammonium salts or amine salts.

By way of specific examples, there may be mentioned:

as oxides: $Rh_2O$, $Rh_2O_3$, $RhO_2$ and $RhO_3$;

as salts of inorganic hydracids: rhodium chloride $RhCl_3$, rhodium bromide $RhBr_3$, rhodium iodide $RhI_3$, rhodium sulfide $Rh_2S_3$, rhodium selenide $Rh_2Se_5$ and rhodium telluride $Rh_2Te_5$;

as salts of inorganic oxyacids: rhodium sulfite $Rh_2(SO_3)_3$, rhodium sulfate $Rh_2(SO_4)_3$, rhodium nitrate $Rh(NO_3)_3$, rhodium perchlorate $Rh(OH)_2ClO_4$ and rhodium selenate;

as salts of carboxylic acids: rhodium acetate $Rh(CH_3CO_2)_3$ and rhodium oxalate $Rh_2(C_2O_4)_3$;

as salts of heteropolyacids containing rhodium: sodium rhodium hexachloride $Na_3[RhCl_6]$, potassium rhodium hexachloride $K_3[RhCl_6]$, barium rhodium hexachloride $Ba_3[RhCl_6]_2$, ammonium rhodium hexachloride $(NH_4)_3[RhCl_6]$, sodium rhodium hexabromide $Na_3[RhBr_6]$, monomethylammonium rhodium phentachloride $(NH_3CH_3)_2[RhCl_5]$ and trimethylammonium rhodium hexachloride $[NH(CH_3)_3]_3[RhCl_6]$.

As other derivatives which can be employed to carry out the process of the invention there may furthermore be mentioned the carbonyl derivatives of rhodium such as rhodium tricarbonyl $Rh(CO)_3$, rhodium tetracarbonyl $[Rh(CO)_4]_2$, the compound $Rh_4(CO)_{11}$, and the halogencarbonyl derivatives of rhodium such as rhodium dicarbonyl chloride $[Rh(CO)_2Cl]_2$, rhodium dicarbonyl bromide $[Rh(CO)_2[Br$ and rhodium dicarbonyl iodide $[Rh(CO)_2]I$.

Other inorganic or organic derivatives which are also suitable are the complex salts of rhodium obtained from the salts mentioned above, especially those of trivalent rhodium, and from monodentate or polydentate ligands. In this context, there may be mentioned the oxygen-containing bidentate ligands of the $\beta$-diketone [acetylacetone] type, the nitrogen-containing monodentate ligands of the type of an alkylamine or nitrogen-containing heterocyclic compound [pyridine] and the nitrogen-containing bidentate ligands of the type of an alkyldiamine and aryldiamine or a nitrogen-containing heterocyclic base [2,2'-dipyridyl and 1,10-phenanthroline]. The bidentate ligands of the type of a diethylenic hydrocarbon of aliphatic or cycloaliphatic origin [cyclopentadiene or 1,5-cyclooctadiene] are also suitable.

As non-limiting examples of complex salts of rhodium, there may be mentioned rhodium-III acetylacetonate, rhodium trichlorotriethylamine $[RhCl_3(C_2H_5NH_2)_3]$, rhodium dichlorodiethylenediamine chloride $[RhCl_2(NH_2CH_2CH_2NH_2)_2]Cl$, rhodium triethylenediamine chloride $[Rh(NH_2CH_2CH_2NH_2)_3]Cl_3$, rhodium-III trichlorotripyridine $(Rhcl_3(C_5H_5N)_3]$, rhodium-III dichlorotetrapyridine chloride $[RhCl_2(C_5H_5N)_4]Cl$, rhodium-III dichloro-didipyridyl chloride $[RhCl_2(Dipy)_2]Cl$, rhodium-III tridipyridyl chloride $[Rh(Dipy)_3[Cl_3$, Rhodium-III dicyclopentadienyl nitrate $[Rh(C_5H_5)_2]NO_3$, rhodium-III dicyclopentadienyl tribromide $[Rh(C_5H_5)_2]Br_3$ and rhodium-III cyclooctadienyl chloride $[Rh(C_8H_{12})Cl]_2$.

The compounds based on rhodium which are preferably used in carrying out the process according to the invention are: the oxides of rhodium, the rhodium salts of inorganic hydracids, the rhodium salts of inorganic oxyacids, the rhodium salts of monocarboxylic or polycarboxylic aliphatic acids, the carbonyl derivatives of rhodium, the halogenocarbonyl derivatives of rhodium and the complex salts of rhodium obtained from the salts mentioned above and from monodentate or polydentate ligands.

A group of compounds based on rhodium which is particularly suitable for carrying out the invention consists of: rhodium oxide $Rh_2O_3$, rhodium chloride $RhCl_3$, rhodium bromide $RhBr_3$, rhodium sulfate $Rh_2(SO_4)_3$, rhodium nitrate $Rh(NO_3)_3$, rhodium acetate $Rh(CH_3CO_2)_3$, rhodium tetracarbonyl $[Rh(CO)_4]_2$, trivalent rhodium acetylacetonate, rhodium cyclooctadienyl chloride $[Rh(C_8H_{12})Cl]_2$ and rhodium dicarbonyl chloride $[Rh(CO)_2Cl]_2$.

It has been found that the use, as a catalyst system, of an aqueous solution of a phosphine of the formula (I) containing either metallic rhodium or a rhodium derivative, such as those mentioned above, renders it possible to obtain yields of aldehyde products which are as high as those provided by the prior art processes previously described, and which results from only very slight occurrence of side reactions such as the hydrogenation of the olefin to the saturated hydrocarbon and the hydrogenation of the aldehyde to the alcohol.

It has furthermore been found that the selectivity of the reaction, measured by the percentage of linear isomers contained in the aldehyde compounds formed from linear olefins having a terminal double bond, such as propylene or 1-hexene, can be as much as 90% and even in excess thereof. It should be mentioned in this context, especially in the case of propylene, that the achievement of such selectivities does not require the use of large quantities of compounds based on trivalent phosphorus, diametrically contrary to the processes of the prior art; these trivalent phosphorus compounds are expensive products and it is important to use as little of same as possible in order not to detract from the economic value of such a process.

Another advantage associated with the process of the present invention resides in the ease with which the hydroformylation products can be separated from the reaction mixture; in fact, at the end of the reaction the oxygen-containing products which are formed are simply decanted or extracted where necessary after having filtered the reaction mixture. Furthermore, if the rhodium is employed in the form of a water-soluble derivative or a derivative capable of passing into aqueous solution under the reaction conditions, the residual aqueous phase, after decanting or extracting the ultimate reaction products, can easily be used, in the state in which it is found, for catalyzing a fresh hydroformylation reaction, and it has also been found in this context that this aqueous solution can be recycled without observing the appreciable loss of a single constituent insofar as the catalyst system is concerned, especially a loss of rhodium, and hence without observing a loss of activity of the catalyst solution.

The catalyst solution used for the hydroformylation can be preformed before introducing same into the reaction zone, for example, by addition of the appropriate amount of rhodium, either in metallic state or in the form of a derivative, to the aqueous solution of the phosphine of the formula (I), the process being carried out, if appropriate, under an atmosphere of hydrogen and, where necessary, of carbon monoxide. It is also possible to start from rhodium in the selected form, from the sulfonated phosphine and from water, and to prepare the catalyst solution in situ by simple mixing of these various constituents.

The amount of olefinic compound used in the subject reaction mixture is not critical.

The amount of rhodium employed, whether in metallic state or in the form of a derivative, is so selected that the number of gram atoms of elementary rhodium which are introduced into one liter of the reaction solution is between 0.0001 and 0.5 and preferably between 0.001 and 0.1.

The amount of sulfonated phosphine of the formula (I) which is used to prepare the reaction solution is so chosen that the number of mols of this compound relative to one gram atom of elementary rhodium is between 1 and 30, preferably between 1.5 and 10.

It too has been found that in certain cases a certain acidity can develop during the hydroformylation reaction, especially if the rhodium-based compounds used are those containing halogen atoms. It is advantageous if the pH of the aqueous catalyst solution is controlled such as not to fall below 2. As a general rule, the pH is maintained at a value of between 2 and 13, and preferably between 4 and 10.

The suitable pH can be obtained by carrying out the reaction in the presence of a defined amount of a suitable basic agent such as, for example, a hydroxide, a carbonate or a borohydride of an alkali metal; in this context, NaOH, $Na_2CO_3$ or $NaBH_4$ may be mentioned.

The reaction can also be carried out in the presence of a buffer mixture containing salts of inorganic oxyacids, the nature and proportions of which in the mixture are such that the pH of their aqueous solutions is between the above-mentioned values. In this context, suitable systems are: phosphoric acid/monobasic phosphate/-dibasic phosphate of an alkali metal, boric acid/borate of an alkali metal, and carbonate/bicarbonate of an alkali metal. Particularly recommended buffer systems consist of equimolar mixtures of the monobasic phosphate and the dibasic phosphate of sodium or of potassium, or of the carbonate and the bicarbonate of sodium or of potassium.

Though the reaction is preferably carried out in water, it can be advantageous to employ an inert organic solvent and especially a water-miscible solvent, preferably having a boiling point below that of water, used in such amount as to make it possible to increase, where necessary, the solubility of the olefin in the aqueous catalyst solution without, however, rendering the aldehyde products formed miscible with the aqueous phase. Solvents which can be used are linear or branched chain saturated aliphatic monohydroxylic compounds such as methyl alcohol, ethyl alcohol, propyl alcohol and isopropyl alcohol, saturated aliphatic ketones such as acetone, lower aliphatic nitriles such as acetonitrile, as well as the methyl ether of diethylene glycol, and dimethyloxyethane. It is also possible to use a solvent which is immiscible with water such as benzene, toluene, benzonitrile, acetophenone, ethyl ether, propyl ether, isopropyl ether, octane, methyl ethyl ketone and propionitrile.

The temperature at which the reaction is carried out can vary over wide limits. Preferably, it is carried out at moderately elevated temperatures which can vary between 20° C. and 150° C. and preferably between 50° C. and 120° C.

The value of the total pressure of hydrogen and carbon monoxide which is required for carrying out the process can be equal to atmospheric pressure, though higher pressures are preferred; total pressures of between 1 and 200 bars, and preferably of between 10 and 100 bars, are in general very suitable.

The partial pressure of carbon monoxide and hydrogen in the gas mixture employed are such that the molar ratio of carbon monoxide to hydrogen varies between 0.1 and 10, preferably, a molar ratio which varies between 0.2 and 5 is used.

A practical method of carrying out the process of the invention consists of introducing, into a suitable pressure-resistant reactor, either the previously formed aqueous catalyst solution, or the constituents, namely water, phosphine of the formula (I) and rhodium, in the metallic form or in the form of a derivative—of which the aqueous catalyst solution is composed, where appropriate together with the basic compound or the buffer system and the organic solvent, if it is decided to use one. After having purged the reactor by means of an inert gas [nitrogen or argon], the apparatus is closed and the olefin is introduced, the apparatus is then pressurized with carbon monoxide and hydrogen, and the reaction mixture is hence heated to the appropriate temperature. It is equally possible to introduce the synthesis gas after having heated the reactor. The carbon monoxide and the hydrogen can be introduced separately, preferably in the sequence of first introducing the CO and then the $H_2$, or can be introduced as a mixture.

After terminating the reaction, the reactor is cooled to ambient temperature, about 20° C., and the excess gas contained therein released. The contents of the reactor are then withdrawn and thereafter it suffices to isolate the aldehyde products by carrying out—if necessary after having filtered the reaction mixture [especially if rhodium deposited on a support is used]—a decantation and, if appropriate, a wash with a suitable solvent such as, for example, diethyl ether, benzene or toluene. It is also possible to separate the aldehyde products from the reaction mixture, if necessary after filtration, by extraction with the aid of one of the aforementioned solvents. Though decantation and extraction are preferred methods of treatment, it is also possible to employ distillation techniques for isolating the aldehyde products formed.

The residual aqueous solution can be recycled into the reactor in order to catalyze a fresh hydroformylation reaction. The process according to the invention is very particularly suitable for being carried out continuously.

In order to further illustrate the present invention and the advantages thereof, the following specific examples are given, it being understood that same are intended only as illustrative and in no wise limitative.

EXAMPLE 1

The following were introduced into a 500 $cm^3$ stainless steel autoclave equipped with a knock-type agitation system and connected to a reserve of gas under pressure, containing an equimolecular mixture of $CO+H_2$;

0.25 g (0.0005 mol) of rhodium cyclooctadienyl chloride $[Rh(C_8H_{12})Cl]_2$, representing 0.001 gram atom of Rh, 2.26 g of the trisodium salt of tri(sulfophenyl)phosphine, containing 80% by weight of pure salt (0.003 mol), and 20 $cm^3$ of a deaerated aqueous solution of a buffer mixture of the composition: 0.025 mol per liter of $Na_2HPO_4$/0.025 mol per liter of $KH_2PO_4$ (pH fixed at about 7).

The reactor was purged for 30 minutes with nitrogen and 50 g (1.19 mols) of propylene were then introduced. The agitation was started and the contents of the autoclave were heated to 80° C. A pressure of 50 bars was then established with the equimolecular mixture of $CO+H_2$ and the agitation was continued while maintaining the temperature and the pressure at the aforementioned values for 24 hours.

At the end of this time, the autoclave was cooled to 20° C. and then degassed, taking care to recover the gas phase in a receptacle containing 100 $cm^3$ of toluene, and cooled to −80° C. by means of a mixture of acetone and solid carbon dioxide. The condensable fraction, dissolved in the toluene, was studied by vapor phase chromatographic analyses and by chemical determinations (the butanals were determined by oximation); it was found that the fraction contains propane (0.008 mol; 0.36 g), propylene (0.171 mol; 7.2 g), n-butanal (0.01 mol; 0.7 g) and iso-butanal (0.0028 mol; 0.2 g). The non-condensable fraction contained solely carbon monoxide and hydrogen.

After degassing, 100 $cm^3$ of toluene were added the contents of the autoclave and the mixture was then introduced into a decantation apparatus. The organic layer was separated off and the residual aqueous phase was washed 3 times, each time with 100 $cm^3$ of toluene. The combined toluene phases were studied by vapor phase chromatographic analyses and by chemical determinations (oximation); it was thus found that they contain a mixture of propane (0.001 mol; 0.046 g), propylene (0.024 mol; 1 g), n-butanal (0.838 mol; 60.4 g) and iso-butanal (0.125 mol; 9 g).

Finally, the reaction balance was found to be the following:

| | |
|---|---|
| Propylene recovered | 8.2 g |
| Degree of conversion of the propylene | 84% |
| (n- + iso-)butanals formed | 70.3 g |
| Yield of(n- + iso-)butanals relative to the propylene consumed | 98% |
| Selectivity: % $\frac{\text{n-butanal}}{\text{(n- + iso-)butanals}}$ | 87% |

Preparation of the sodium salt of tri(sulfophenyl)phosphine

One liter of oleum containing 20% by weight of sulfur trioxide was introduced into a 2 liter flask equipped with a central stirrer system, a thermometer and a reflux condenser and cooled externally by means of an ice bath, and the flask was then flushed by means of argon. The stirring was started and 100 g of triphenylphosphine was then introduced gradually over the course of about 2 hours while maintaining the reaction temperature at between 20° C. and 40° C. during the operation. Once the addition was complete, the stirring of the mixture was continued at the aforementioned temperature for a period randing from 15 to 25 hours. The reaction mixture was then cooled to 10° C. after which it was poured carefully into a 10 liter flask containing 2,000 $cm^3$ of water cooled to 0° C. 1,500 g of sodium hydroxide pellets were added to the resulting mass while maintaining the temperature of the mixture at a value below 20° C. during the addition. The solution thus obtained was left for several hours at ambient temperature, approximately 20° C.

At the end of this time, the sodium salts which had precipitated were recovered by filtration and then washed twice with 1,500 $cm^3$ of ice water; the combination of the filtrate and of the wash waters was concentrated to a volume of 1,500 $cm^3$ by heating under reduced pressure.

The precipitate obtained at the end of the concentration stage was filtered and then washed 3 times with 300 $cm^3$ of ice water; the combination of the filtrate and of the wash waters has concentrated to a volume of 500 $cm^3$ by heating under reduced pressure.

500 $cm^3$ of methanol were added to the above concentration residue and the precipitate which had appeared was then filtered off and washed with 500 $cm^3$ of a mixture of $CH_3OH$ (50%)/$H_2O$ (50%). The combination of the filtrate and of the wash solution was then concentrated to a volume of 200 $cm^3$, after which 1,000 $cm^3$ of methanol were added. The precipitate formed was filtered off and then washed 6 times with 1,000 $cm^3$ of methanol heated to 60° C.; the mother liquors from the filtration and from the wash solution were combined and then evaporated to dryness. The evaporation residue was introduced into 500 $cm^3$ of absolute ethanol. The solution obtained was filtered and the solid on the filter was then washed with 20 $cm^3$ of ethanol, after which it was dried at 25° C. under reduced pressure (0.1 mm Hg) for 30 hours. 172 g of a white solid remain.

The results of the study of this solid by elementary analyses (determination of the contents of C, H, S and P), by infra-red spectroscopy, by nuclear magnetic resonance and by chemical determination of the trivalent phosphorus (iodometry) indicate that the solid was a mixture of trisodium salts of tri(sulfophenyl)phosphine and of tri(sulfophenyl)-phosphine oxide.

The composition of the mixture of salts varies with the temperature and the duration of the sulfonation reaction. If the triphenylphosphine is added at a temperature of about 30° C. and the stirring of the mixture is then continued at this temperature for about twenty hours, a mixture containing 80% by weight of the sodium salt of tri(sulfophenyl)phosphine and 20% by weight of the sodium salt of tri(sulfophenyl)phosphine oxide is isolated. If the process is carried out at 40° C. for 24 hours, the mixture of salts obtained contains 60% by weight of the sodium salt of tri(sulfophenyl)phosphine.

EXAMPLES 2 to 5

The following were introduced into a 125 $cm^3$ stainless steel autoclave equipped with a knock-type agitation system:

0.05 g (0.0001 mol) of $[Rh(C_8H_{12})\ Cl]_2$, representing 0.0002 gram atom of Rh, 0.06 g of the trisodium salt of tri(sulfophenyl)-phosphine, prepared as indicated in Example 1 and containing 60% by weight of pure salt (0.0006 mol), 4 $cm^3$ of deaerated water (Example 2) and 4 $cm^3$ of a deaerated aqueous solution of a buffer mixture consisting of 0.1 mol/liter of $NaHCO_3$ and of 0.1 mol/liter of $Na_2CO_3$ (pH fixed at about 10; Example 3); 4 $cm^3$ of a deaerated aqueous solution of a buffer mixture consisting of 0.09 mol/liter of $H_3PO_4$ acid, 0.025 mol/liter of $Na_2HPO_4$ and 0.025 mol/liter of $KH_2PO_4$ (pH fixed at about 2.2; Example 4); or 4 $cm^3$ of a deaerated aqueous solution of a buffer mixture consisting of 0.025 mol/liter of $Na_2HPO_4$ and of 0.025 mol/liter of $KH_2PO_4$ (pH fixed at about 7; Example 5).

The reactor was purged for 30 minutes with argon, 10 g (0.238 mol) of propylene were then introduced and a pressure of 40 bars was established with an equimolecular mixture of $CO+H_2$. In these examples, the hydroformylation was carried out with an amount of olefin which was in excess of the amount of synthesis gas introduced; the molar ratio of propylene/CO or $H_2$ was about 2.7.

The autoclave was then heated to 80° C. and agitated for 4 hours at this temperature.

The treatment which was carried out was that which has been described in Example 1.

More particularly, the autoclave was cooled to 20° C. and then degassed, and the condensable gaseous fraction was recovered in a receptacle containing 20 $cm^3$ of toluene, cooled to −80° C., and was studied by vapor phase chromatographic analyses. The (residual) contents of the autoclave were introduced into a decantation apparatus. After separating the organic layer, the aqueous phase was washed twice with 20 $cm^3$ of toluene. The combined toluene phases were analyzed by vapor phase chromatography.

In the case of Example 5 only, the residual aqueous phase was reintroduced into the autoclave and a fresh hydroformylation reaction of 10 g of propylene was carried out under the conditions of Example 5 (recycle 1). A second recycle of the catalyst solution, after treatment, was carried out (recycle 2).

The results are summarized in the table which follows:

TABLE 1

| | | | | 5 | | |
|---|---|---|---|---|---|---|
| EXAMPLES | 2 | 3 | 4 | Hydro-for-mylation | Re-cycle 1 | Re-cycle 2 |
| (n- + iso-)butanals formed | 1.9 g | 4.4 g | 3.6 g | 4.5 g | 4.1 g | 3.9 g |
| Yield of(n- + iso-) butanals/CO or $H_2$ employed | 30% | 70% | 57% | 71% | 65% | 62% |
| Selectivity: % $\frac{\text{n-butanal}}{\text{(n- + iso-)butanals}}$ | 87% | 92% | 87% | 92% | 88% | 89% |

EXAMPLE 6

Example 5 was repeated without recycling the aqueous catalyst solution, and employing:

0.005 g (0.00001 mol) of $[Rh(C_8H_{12}(Cl]_2$, representing 0.00002 gram atom of Rh, and 0.2 g of the trisodium salt of tri(sulfophenyl)phosphine, prepared as indicated in Example 1 and containing 60% by weight of pure salt (0.002 mol).

After 4 hours of reaction the results were as follows: (n-+iso-)butanals formed: 3 g; yield of (n-+iso-)butanals/CO or $H_2$ employed: 48%, of n-butanal/(n-+iso-butanals: 84%.

EXAMPLES 7 to 10

Example 5 was repeated without recycling the aqueous catalyst solution, and employing:

0.77 g of the Ba salt of tri(sulfophenyl)phosphine, containing 55% by weight of pure salt, representing 0.0006 mol (Example 7), 0.89 g of the tetraethylammonium salt of tri(sulfophenyl)phosphine, containing 60% by weight of pure salt, representing 0.0006 mol (Example 8), 0.30 g of the Na salt of di(sulfophenyl)phenylphosphine, representing 0.0006 mol (Example 9), or 0.40 g of the trisodium salt of tri(sulfophenyl)phosphine, containing 95% by weight of pure salt, representing 0.0006 mol (Example 10).

TABLE II

| EXAMPLES | 7 | 8 | 9 | 10 |
|---|---|---|---|---|
| (n- + iso-)butanals formed | 5.57 g | 6.21 g | 3.83 g | g |
| Yield of(n- + iso-)butanals/ CO or $H_2$ employed | 89% | 98% | 61% | 71% |
| Selectivity: % $\frac{\text{n-butanal}}{\text{(n- + iso-)butanal}}$ | 90% | 91% | 84% | 96% |

Preparation of the barium salt and of the tetraethylammonium salt of tri(sulfophenyl) phosphine The desired amount of the trisodium salt of tri(sulfophenyl)phosphine, prepared as indicated in Example 1 and containing 60% by weight of pure salt (about 1 mol/liter), was dissolved in water and the solution obtained was then passed over a column containing an excess (about 4 times the theoretical amount) of a strong acid ion exchange resin (sulfonic acid), known under the tradename of AMBERLITE IR-120H, and finally the column was eluted with water. The resulting acid aqueous solution was neutralized with Ba hydroxide or tetraethylammonium hydroxide and was then evaporated to dryness by heating under reduced pressure.

Preparation of the disodium salt of di(sulfophenyl)phenyl-phosphine and of the trisodium salt of tri(sulfophenyl) phosphine of 95% purity These two sulfonated phenylphosphines are isolated, separately, at the end of the following reaction:

100 $cm^3$ of oleum containing 20% by weight of sulfur trioxide were introduced into an 0.5 liter flask equipped with a central stirrer system, a thermometer and a reflux condenser and cooled externally by means of an ice bath, and the flask was then flushed with agron. The stirring ws commenced and 10 g of triphenylphosphine were then gradually introduced while maintaining the reaction temperature at 25° C. during operation. Stirring was continued at this temperature for 17 hours. The reaction mixture was then introduced into a receptacle containing 1,000 g of ice, after which it was neutralized with 400 $cm^3$ of a 10 N aqueous NaOH solution.

The salts which precipitated were filtered off and then dried to constant weight. The resulting solid, weighing 18 g, was introduced into 65 $cm^3$ of water which was heated to a boil; the insoluble particles were filtered off hot and the filtrate was left to cool to 20° C. The solid which precipitated was filtered off, washed with 10 $cm^3$ of cold water and then dried at 25° C., under 0.1 mm Hg, for 30 hours, 8 g of the pure disodium salt of di(sulfophenyl)phosphine were thus recovered. The analyses carried out to identify this product were in particular elementary analyses, infra-red spectroscopy, nuclear magnetic resonance and iodometric determination of the trivalent phosphorus.

The filtrate from the reaction mixture, after neutralization with sodium hydroxide solution, was evaporated to dryness by heating under reduced pressure. The solid obtained was taken up in 2,000 $cm^3$ of absolute ethanol heated to 80° C.; the insoluble particles were filtered off hot, and the filtrate was concentrated by evaporation to a volume of 15 $cm^3$. 200 $cm^3$ of cold absolute ethanol were added; the precipitate formed was filtered off, washed with ethanol and then dried at 25° C. under 0.1 mm Hg for 30 hours. 6.8 g of the trisodium salt of tri(sulfophenyl)phosphine, containing 95% by weight of pure salt, were thus recovered. The remainder consisted of the sodium salt of tri(sulfophenyl)phosphine oxide.

EXAMPLES 11 to 14

The following were introduced into a 125 $cm^3$ stainless steel autoclave equipped with a knock-type agitation system:

rhodium in a form other than $[Rh(C_8H_{12})Cl]_2$, namely $RhCl_3.4H_2O$ (Example 11), $Rh_2O_3.5H_2O$ (Example 12), rhodium in the form of a catalyst containing 4.95% by weight of the metal deposited on charcoal (Example 13) or $Rh(NO_3)_3$ (Example 14), the Na salt of tri(sulphophenyl)phosphine, prepared as indicated in Example 1 and containing 60% by weight of pure salt, and 4 $cm^3$ of a deaerated aqueous solution of a buffer mixture which fixes the pH at about 7.

Thereafter the procedure indicated for Example 2 and the subsequent examples was followed as regards the introduction of propylene and synthesis gas, and the treatment carried out.

The results are summarized in the table which follows:

TABLE III

| EXAMPLES | 11 | 12 | 13 | 12 |
|---|---|---|---|---|
| Nature of the rhodium gram atom Rh | $RhCl_3.4H_2O$ 0.0002 | $Rh_2O_3.5H_2O$ 0.0002 | Rh/charcoal 0.0002 | $Rh(NO_3)_3$ 0.0002 |
| Mols of trisulfonated phosphine | 0.0012 | 0.0012 | 0.0006 | 0.0012 |
| Buffer mixture | 0.25 mol/l of $Na_2HPO_4$ + 0.25 mol/l of $KH_2PO_4$ | 0.025 mol/l of $Na_2HPO_4$ + 0.025 mol/l of $KH_2PO_4$ | 0.025 mol/l of $Na_2HPO_4$ + 0.025 mol/l of $KH_2PO_4$ | 0.25 mol/l of $Na_2HPO_4$ + 0.25 mol/l of $KH_2PO_4$ |
| (n- + iso-)butanals formed | 1.8 g | 0.9 g | 1.98 g | 1.85 g |
| Yield of (n- + iso-)butanals/CO or $H_2$ employed | 29% | 13% | 31% | 30% |
| Selectivity $\% \frac{\text{n-butanal}}{\text{(n- + iso-)butanals}}$ | 89% | 82% | 88% | 83% |

EXAMPLES 15 to 17

These examples relate to the hydroformylation of 1-hexene. In these examples, the catalyst solution was preformed before introducing same into the autoclave.

(a) The following catalyst solution were prepared:

Solution 1: 0.307 g of the Na salt of tri(sulfophenyl)-phosphine, prepared as indicated in Example 1 and containing 60% by weight of pure salt (representing 0.000324 mol) were dissolved, in a glass reactor, under stirring and an argon atmosphere, in 5 $cm^3$ of a deaerated aqueous solution of a buffer mixture of the composition 0.025 mol/liter of $Na_2HPO_4$/0.025 mol/liter of $NaH_2PO_4$, and thereafter 0.027 g (0.000054 mol) of $[Rh(C_8H_{12})Cl]_2$, representing 0.000108 gram atom of Rh, were added. Dissolution occurred within a few minutes.

Solution 2: 0.307 g of the sulfonated phosphine used to prepare solution 1 were dissolved in 5 $cm^3$ of an aqueous-alcoholic solution formed from 2.5 $cm^3$ of the buffer mixture employed for solution 1 and from 2.5 $cm^3$ of ethanol, and 0.027 g (0.000054 mol) of $[Rh(C_8H_{12})Cl]_2$, representing 0.000108 gram atom of Rh, were then added.

Solution 3: this was prepared like solution 2, but using 0.021 g (0.000054 mol) of rhodium dicarbonyl chloride, $[Rh(CO)_2Cl]_2$, representing 0.000108 gram atom of Rh.

(b) Hydroformylation:

The following were introduced into a 150 $cm^3$ autoclave equipped with a central stirrer system and connected to a reserve of synthesis gas under pressure, wherein the ratio of molar amounts of CO and $H_2$ is 0.22: the catalyst solution 1 followed by 6.72 g (0.08 mol) of 1-hexene (Example 15), or the catalyst solution 2 followed by 6.72 g (0.08 mol) of 1-hexene (Example 16), or the catalyst solution 3 followed by 6.72 g (0.08 mol) of 1-hexene (Example 17).

The stirrer was started and the contents of the autoclave were heated to 100° C. A pressure of 55 bars was then established with the aforementioned mixture of $CO+H_2$, and stirring was continued while maintaining the temperature and the pressure at the aforementioned values for a defined period of time.

After cooling to 20° C., the autoclave was degassed and its contents were left to stand until the solid separated out.

The reaction balance was calculated on the basis of vapor phase chromatography analyses of the fraction obtained by degassing and of the organic phase obtained by decanting.

The results are summarized in the table which follows:

TABLE IV

| EXAMPLES | 15 | 16 | 17 |
|---|---|---|---|
| Duration | 21 hours | 20 hours | 5 hours |
| Degree of conversion of 1-hexene | 15% | 79% | 61% |
| Yield of n-heptanal + 2-methyl-hexanal relative to hexane consumed | 71% | 94% | 91% |
| Selectivity: $\% \frac{\text{n-heptanal}}{\text{n-heptanal + 2-methyl-hexanal}}$ | 92% | 91% | 85% |

EXAMPLE 18

Example 17 was repeated, but 2-hexene was alternatively used. After treatment, the aldehyde products isolated were n-heptanal, 2-methyl-hexanal and 2-ethyl-pentanal. The following reaction balance was calculated: degree of conversion of 2-hexene after 5 hours' reaction: 9.8%; yield of aldehyde products formed, relative to the olefin consumed: 98%, selectivity:

$$\% \frac{\text{n-heptanal + 2-methyl-hexanal}}{\text{aldehyde products}} = 67\%$$

EXAMPLE 19

Preparation of the monosodium salt of (m-sulfophenyl)-diphenylphosphine dihydrate This phosphine was prepared in accordance with the method described in J. Chem. Soc., 276, 288 (1958), J. Chatt. The phosphine was soluble to the extent of 80 g/l in water at 20° C. and can be isolated simply by diluting the reaction mixture with an equal weight of ice, neutralizing same with concentrated sodium hydroxide solution and then adding methanol in such manner that the ratio, by volume, of methanol to water was 10. The sodium sulfate which precipitated was filtered off. The filtrate was concentrated so as to recover the methanol; the monosodium salt of (m-sulfophenyl)diphenylphosphine precipitated. The supernatant solution contained a little sodium sulfate and disodium salt of di(sulfophenyl)phenylphosphine and a portion of the monosodium salt of (m-sulfophenyl)-diphenylphosphine.

The results of the study of this solid by elementary analyses (determination of the contents of C, H, S and P), by infra-red spectroscopy, by nuclear magnetic resonance and by chemical determination of the trivalent phosphorus by means of iodine indicated that it was indeed a m-sulfonated product.

Hydroformylation:

The following were introduced into a 125 $cm^3$ stainless steel autoclave equipped with a knock-type agitation system:

0.050 g (0.0001 mol) of $[Rh(C_8H_{12}(Cl]_2$, representing 0.0002 gram atom of Rh, 0.338 g of the monosodium salt of (m-sulfophenyl)diphenylphosphine dihydrate, 4 $cm^3$ of a deaerated aqueous solution of a buffer mixture consisting of 0.025 mol/l of $Na_2HPO_4$ and of 0.025 mol/liter of $KH_2PO_4$ (pH fixed at about 7).

The reactor was purged with argon for 30 minutes, 10 g of propylene were then introduced and a pressure of 40 bars was established with an equimolecular mixture of $CO+H_2$.

The autoclave was then heated to 80° C. and stirred for 4 hours at this temperature. The gas was released, when cold, into a trap containing 20 g of toluene at −80° C., and the autoclave was then opened. A light chestnut-colored homogeneous aqueous layer, and a colorless supernatant organic layer were observed. This system was taken up in toluene. The toluene, made up to 100 $cm^3$, contains 2.94 g of butanals, of which 2.48 g were n-butanal and 0.46 g were isobutanal, representing a 90% selectivity with respect to the linear product.

EXAMPLE 20

Preparation of the trisodium salt of tri(m-sulfophenyl)-phosphine dihydrate of greater than 95% purity This phosphine was prepared in accordance with a process analogous to that of Example 7, the sulfonation being carried out at a temperature of between 18° and 20° C. for 48 hours. It was indisputably shown by analysis of the nuclear magnetic resonance spectra of the $^{13}C$ nucleus on a BRUCKER WH 90 spectrometer at a frequency of 22.63 MHZ that the sulfonate substitution was in the meta-position. The principal impurity was the trisodium salt of tri(m-sulfophenyl)phosphine oxide which can be prepared by oxidation of the corresponding phosphine with iodine, or by sulfonation of triphenylphosphine oxide.

Hydroformylation in the presence of toluene:

The following were introduced into a 125 $cm^3$ stainless steel autoclave equipped with a knock-type agitation system:

0.050 g (0.0001 mol) of $[Rh(C_8H_{12})Cl]_2$, representing 0.0002 gram atom of Rh, 0.380 g of the trisodium salt of tri(m-sulfophenyl)-phosphine dihydrate of 95% purity, 4 $cm^3$ of the buffer solution of Example 1 and 10 $cm^3$ of toluene.

The reactor was purged for 30 minutes with argon, 10 g of propylene were then introduced, and a pressure of 42 bars was established with an equimolecular mixture of $CO+H_2$.

The autoclave was then heated to 80° C. and was stirred for 18 hours at this temperature. When cold, the gas was released into a trap containing 20 g of toluene. An aqueous layer of less than about 3.9 to 4 $cm^3$ and a supernatant solution containing the toluene and 5.12 g of butanal were observed; in the latter, 4.71 g were n-butanal and 0.41 g were isobutanal, representing a selectivity of 92% with respect to the linear product.

EXAMPLE 21

The same experiment, in the absence of toluene, yields, on discharge from the reactor, a colorless supernatant phase containing 92% of n-butanal and 8% of isobutanal and trace of propylene. No rhodium was detected by emission spectrum analysis of the supernatant phase (sensitivity 0.5 ppm).

EXAMPLE 22

Preparation of a mixture of the trisodium salt of (tri-m-sulfophenyl)phosphine and of the disodium salt of di(sulfophenyl) phenylphosphine 1,900 g of oleum containing 20% of sulphur trioxide, followed by 100 g of triphenyl phosphine, were introduced into a glass reactor without exceeding 20° C., and the mixture was then left under stirring for 63 hours at 20° C. The material was then added slowly to 3 kg of ice and was neutralized with 966 g of sodium hydroxide flakes followed by 1,190 $cm^3$ of 10 N sodium hydroxide solution. At the end of the neutralization, a slurry was obtained, which was filtered. The solid, which represents 1,850 g of hydrated sodium sulphate, was washed with $4\times500$ $cm^3$ of methanol. By successive concentrations and addition of methanol, 192 g of a mixture containing the following were obtained:

13.3% of sodium sulphate pentahydrate, 49.5% of the trisodium salt of tri(m-sulfophenyl)-phosphine, and 37.2% of the monosodium salt of di(m-sulfophenyl)-phosphine.

(The content of trivalent phosphorus relative to the total phosphorus is 92%, and the phosphines contain 8% of disulfonated and trisulfonated phosphine oxide).

The methanol was recovered by distillation.

Hydroformylation:

The experiment was carried out in accordance with Example 2, 0.450 g of the mixture of phosphines being introduced in place of the trisodium salt of tri(m-sulfophenyl)-phosphine. After the reaction, the toluene solution contains 4.90 g of butanals, of which 4.31 g were n-butanal and 0.59 g were isobutanal, representing a selectivity of 88% with respect to the branched product.

EXAMPLE 23

Preparation of the disodium salt of di(m-sulfophenyl)-phenyl-phosphine

This phosphine was isolated from the mixture of phosphines obtained in Example 22.

Hydroformylation in the presence of toluene:

The following were introduced into a 125 $cm^3$ stainless steel autoclave equipped with a knock-type agitation system:

0.050 g (0.0001 mol) of $[Rh(C_8H_{12})Cl]_2$, representing 0.002 gram atom of Rh, 0.300 g of the disodium salt of di(meta-sulphophenyl)-phenylphosphine, 4 $cm^3$ of the buffer solution of Example 1 and 10 $cm^3$ of toluene.

The reactor was purged for 30 minutes with argon, 10 g of propylene were then introduced, and a pressure of 40 bars was established with an equimolecular mixture of $CO+H_2$.

The autoclave was then heated to 80° C. and stirred for 8 hours at this temperature. When cold, the gas was released into a trap containing 20 g of toluene. An aqueous layer of less than about 3.9 to 4 $cm^3$ and a supernatant solution containing the toluene and 4 g of butanals are observed; of the latter, 3.56 g were n-butanal and 0.54 g were isobutanal, representing a selectivity of 87% with respect to the linear product.

EXAMPLE 24

Hydroformylation of butadiene:

The following were introduced into a 125 $cm^3$ stainless steel autoclave equipped with a knock-type agitation system:

0.050 g (0.001 mol) of $[Rh(C_8H_{12}(Cl]_2$, representing 0.0002 gram atom of Rh, 0.380 g of the trisodium salt of tri(m-sulfophenyl)-phosphine dihydrate, of more than 95% purity, and 4 $cm^3$ of the buffer solution of Example 1.

The reactor was purged with argon for 30 minutes, and 13 g of butadiene were then introduced, followed by sufficient equimolecular mixture of $CO+H_2$ to establish a pressure of 20 bars. The autoclave was then heated to 80° C. and a constant total pressure of 50 bars was established immediately by means of an equimolecular mixture of $CO+H_2$ coming from a reserve (vessel) at 100 bars, with a pressure-reducing valve.

After 17 hours of reaction, the gas was slowly released into a trap containing toluene, initially cold, and then at 70° C.; 0.8 g of butadiene were recovered. The reaction mixture in the autoclave contained 2 liquid phases, namely, a lower aqueous phase, color brown-red, of about 4 $cm^3$, and a colorless upper organic phase of 18.4 g, which contained

| | |
|---|---|
| 75% of $C_5$—aldehydes | 2% of methylbutanal<br>45% of pentanal<br>53% of pentenals |

25% of less volatile products, including some $C_9$ unsaturated monoaldehydes and traces of $C_6$ dialdehyde.

While there have been shown and described and pointed out the fundamental novel features of the invention as applied to the preferred embodiment, those skilled in the art will appreciate the various modifications, changes, additions and omissions in the catalytic hydroformylation of olefins illustrated and described can be made without departing from the spirit of the invention. It is the intention, therefore, to be limited only by the scope of the following claims.

What is claimed is:

1. In a process for the hydroformylation of [linear or branched chain ethylenically unsaturated aliphatic olefins having from 2 to 20 carbon atoms to their corresponding aldehydes] *an olefin to its corresponding aldehyde*, in liquid phase, comprising reacting an olefin with carbon monoxide and hydrogen, the improvement which comprises conducting the hydroformylation reaction in the presence of an aqueous solution of at least one water-soluble phosphine having the following structural formula:

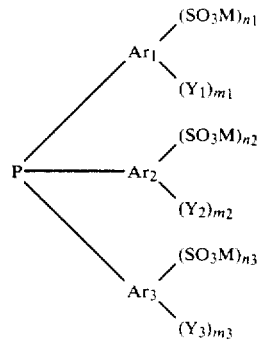

(I)

in which:

$Ar_1$, $Ar_2$ and $Ar_3$, which may be identical or different, represent carbocyclic aryl groups having from 6 to 10 carbon atoms, $Y_1$, $Y_2$ and $Y_3$, which may be identical or different, each represents a radical selected from the group consisting of linear or branched chain alkyl radicals having from 1 to 4 carbon atoms, alkoxy radicals having from 1 to 4 carbon atoms, halogen atoms, the —OH radical, the —C≡N radical, the $—NO_2$ radical, and the radical of the formula $—NR_1R_2$, in which $R_1$ and $R_2$, which may be identical or different, represent a linear or branched chain alkyl radical having from 1 to 4 carbon atoms, M is an inorganic or organic cationic radical selected from the group consisting of the cations derived from the alkali metals, the alkaline earth metals, lead, zine and copper, $NH_4^+$, and $N(R_3R_4R_5R_6)^+$ wherein $R_3$, $R_4$, $R_5$ and $R_6$, which may be identical or different, each represents a linear or branched chain alkyl radical having from 1 to 4 carbon atoms, $m_1$, $m_2$ and $m_3$ are identical or different integers between 0 and 5 and $n_1$, $n_2$ and $n_3$ are identical or different integers between 0 and 3, at least one of the numbers $n_1$, $n_2$ or $n_3$ being greater than or equal to 1, said aqueous solution of the sulfonated aryl phosphate additionally comprising a member selected from the group consisting of metallic rhodium and a rhodium containing compound.

2. The process as defined by claim 1, wherein the at least one phosphine of the formula (I):

$Ar_1$, $Ar_2$ and $Ar_3$ are phenyl, $Y_1$, $Y_2$ and $Y_3$ represent a radical selected from the group consisting of methyl, ethyl, methoxy and ethoxy, and chloro, M represents a cation selected from the group consisting of sodium, potassium, calcium, barium, $NH_4^+$ and the tetramethylammonium, tetraethylammonium, tetrapropylammonium and tetrabutylammonium ions, and $m_1$, $m_2$ and $m_3$ are identical or different integers of between 0 and 3.

3. The process as defined by claim 1, wherein the at least one phosphine of the formula (I) is used, in which $Ar_1$, $Ar_2$ and $Ar_3$ are a phenyl, $m_1$, $m_2$ and $m_3$ are equal to 0, $n_1$, $n_2$ and $n_3$ have a value equal to 0 or 1, the sum $n_1+n_2+n_3$ being between 1 and 3 and the $SO_3H$ groups are in the meta-position.

4. The process as defined by claim 3, wherein the at least one phosphine has the structural formula:

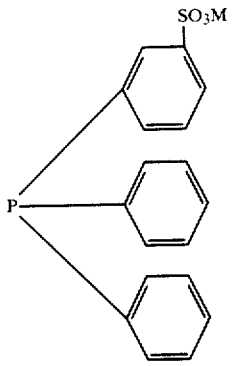

5. The process as defined by claim 3, wherein the at least one phosphine has the structural formula:

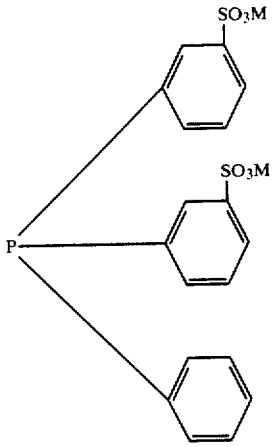

6. The process as defined by claim 3, wherein the at least one phosphine has the structural formula:

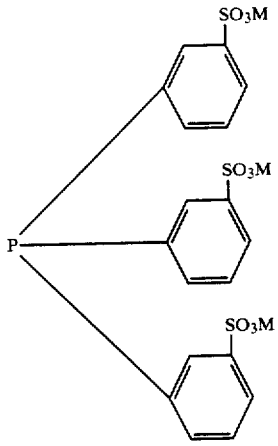

7. The process as defined by claim 3, wherein the aqueous solution comprises a mixture of at least two of the phosphines selected from the group consisting of:

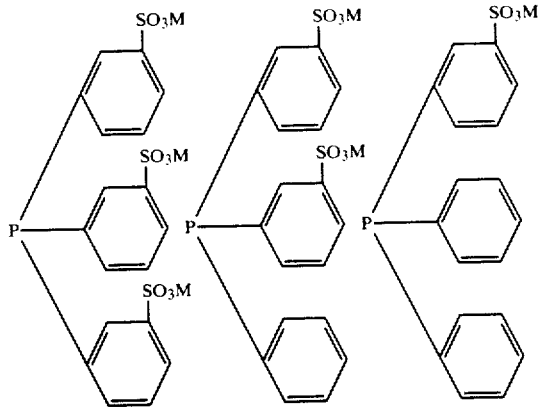

8. The process as defined by claim 3, wherein M is sodium.

9. The process as defined by claim 1, wherein supported metallic rhodium comprises the aqueous solution.

10. The process as defined by claim 9, wherein the metallic rhodium is supported on a member selected from the group consisting of charcoal, calcium carbonate and alumina.

11. The process as defined by claim 1, wherein the rhodium containing compound is employed, the same being selected from the group consisting of the oxides of rhodium, the rhodium salts of inorganic hydracids, the rhodium salts of inorganic oxyacids, the rhodium salts of aliphatic monocarboxylic or polycarboxylic acids, the carbonyl derivatives of rhodium, the halogenocarbonyl derivatives of rhodium, and the complex salts of rhodium obtained from the foregoing salts and from monodentate or polydentate ligands.

12. The process as defined by claim 11, wherein the chloride, bromide, iodide, sulfide, selenide and telluride are employed as rhodium salts of inorganic hydracids, the sulfite, sulfate, nitrate, perchlorate and selenate are employed as rhodium salts of inorganic oxyacids, the acetates, propionate, oxalate and malonate are used as rhodium salts of aliphatic monocarboxylic or polycarboxylic acids, and the complex salts obtained from the foregoing salts and from oxygen-containing bidentate $\beta$-diketone ligands, nitrogen-containing alkylamine or nitrogen-containing heterocyclic monodentate ligands, nitrogen-containing alkyldiamine, aryldiamine or nitrogen-containing heterocyclic bidentate ligands, and aliphatic or cycloaliphatic diethylenic hydrocarbon bidentate ligands, are employed as the complex salts of rhodium.

13. The process as defined by claim 11, wherein the rhodium containing compound is selected from the group consisting of rhodium oxide $Rh_2O_3$, rhodium chloride $RhCl_3$, rhodium bromide $RhBr_3$, rhodium sulfate $Rh_2(SO_4)_3$, rhodium nitrate $Rh(NO_3)_3$, rhodium acetate $Rh(CH_3CO_2)_3$, rhodium tetracarbonyl $[Rh(CO)_4]_2$, rhodium dicarbonyl chloride $[Rh(CO)_2Cl]_2$, trivalent rhodium acetylacetonate and rhodium cyclooctadienyl chloride $[Rh(C_8H_{12})Cl]_2$.

14. The process as defined by claim 1, wherein the amount of rhodium employed, in either the metallic state or in the form of a rhodium containing compound, is selected such that the number of gram atoms of elementary rhodium which are introduced into one liter of the reaction solution is between 0.0001 and 0.5.

15. The process as defined by claim 1, wherein the amount of sulfonated phosphine of the formula (I) which is used to prepare the reaction solution is selected such that the number of mols of this compound relative to one gram atom of elementary rhodium is between 1 and 30.

16. The process as defined by claim 1, wherein the hydroformylation reaction is carried out at a pH of between 2 and 13.

17. The process as defined by claim 1, wherein the hydroformylation reaction is carried out in the presence of a buffer mixture containing salts of inorganic oxyacids, the nature and proportions of which in the mixture are such that the pH of their aqueous solutions is between 2 and 13.

18. The process as defined in claim 1, wherein the hydroformylation reaction is carried out in the presence of a solvent selected from the group consisting of methyl alcohol, ethyl alcohol, propyl alcohol, isopropyl alcohol, acetone, acetonitrile, the methyl ether of diethylene glycol and dimethoxyethane.

19. The process as defined by claim 1, wherein the hydroformylation reaction is carried out in the presence of a solvent selected from the group consisting of benzene, toluene, benzonitrile, acetophenone, ethyl ether, propyl ether, isopropyl ether, octane, methyl ethyl ketone and propionitrile.

20. The process as defined by claim 1, wherein the hydroformylation reaction is carried out at a temperature of between 20° C. and 150° C.

21. The process as defined by claim 1, wherein the hydroformylation reaction is carried out at a total pressure of hydrogen and of carbon monoxide which is between 1 and 200 bars.

22. The process as defined by claim 21, wherein the partial pressures of carbon monoxide and of hydrogen in the gas mixture utilized are such that the molar ratio of carbon monoxide to hydrogen varies between 0.1 and 10.

23. The process as defined by claim 1, wherein a two-phase organic/aqueous liquid reaction mixture is obtained.

24. The process as defined by claim 23, wherein the organic phase of the reaction mixture is separated by decantation from the aqueous phase of said mixture.

25. The process as defined by claim 14, said number of gram atoms of elementary rhodium being between 0.001 and 0.1.

26. The process as defined by claim 15, wherein the number of mols of sulfonated phosphine is between 1.5 and 10.

27. The process as defined by claim 15, the pH being between 4 and 10.

28. The process as defined by claim 17, the pH being between 4 and 10.

29. The process as defined by claim 20, the temperature being between 50° C. and 120° C.

30. The process as defined by claim 21, the total pressure being between 10 and 100 bars.

31. The process as defined by claim 22, said molar ratio varying between 0.2 and 5.

32. The process as defined by claim 11, wherein the rhodium containing compound is selected from the group consisting of rhodium oxide, rhodium oxalate, rhodium selenate, rhodium perchorate, rhodium sulfite, rhodium telluride, rhodium selenide, rhodium iodide, rhodium sulfide, sodium rhodium hexachloride, potassium rhodium hexachloride, barium rhodium hexachloride, ammonium rhodium hexachloride, sodium rhodium hexabromide, monomethylammonium rhodium pentachloride, trimethylammonium rhodium hexachloride, rhodium tricarbonyl, rhodium dicarbonyl bromide, rhodium dicarbonyl iodide, rhodium trichlorotriethylamine, rhodium dichlorodiethylenediamine chloride, rhodium triethylenediamine chloride, rhodium-III trichlorotripyridine, rhodium-III dichlorotetrapyridine chloride, rhodium-III dichlorodidipyridyl chloride, rhodium-III tridipyridyl chloride, rhodium-III dicyclopentadienyl nitrate and rhodium-III dicyclopentadienyl tribromide.

33. The process as defined in claim 1, the olefin hydroformylated being selected from the group consisting of ethylene, propylene, 1-butene, 2-methyl-1-butene, 2-butene, 1-pentene, 2-pentene, 1-hexene, 3-ethyl-1-hexene, 2-propyl-1-hexene, 2-hexene, 1-heptene, 1-octene, 3-octene, 4,4-dimethyl-1-nonene, 1-decene, 2-decene, 6-propyl-1-decene, 3-undecene, 1-dodecene, 5-tetradecene, 1-octadecene and 2-octadecene.

34. The process as defined by claim 1, the olefin hydroformylated having from 2 to 8 carbon atoms.

35. The process as defined by claim 1, the at least one water-soluble phosphine being selected from the group consisting of the alkali metal, alkaline earth metal, ammonium and quaternary ammonium salts of (p-sulfophenyl)diphenylphosphine, (m-sulfo-p-methylphenyl)-di(p-methylphenyl)phosphine, (m-sulfo-p-methoxyphenyl)di(p-methoxyphenyl)phosphine, (m-sulfo-p-chlorophenyl)di(p-chlorophenyl)phosphine, di(p-sulfophenyl)phenylphosphine, di(m-sulfo-p-methylphenyl)(p-methylphenyl)phosphine, di(m-sulfo-p-methoxyphenyl) (p-methylphenyl) phosphine, di(m-sulfo-p-chlorophenyl) (p-chlorophenyl)phosphine, tri(p-sulfophenyl)phosphine, tri(m-sulfo-p-methylphenyl)phosphine, tri(m-sulfo-p-methoxyphenyl)phosphine, tri(m-sulfo-p-chlorophenyl)phosphine, (o-sulfo-p-methylphenyl) (m-sulfo-p-methyl) (m,m'-disulfo-p-methyl)phosphine and (m-sulfophenyl) (m-sulfo-p-chlorophenyl) (m,m'-disulfo-p-chlorophenyl)phosphine.

*36. The process as defined by claim 1, the olefin comprising a linear or branched chain ethylenically unsaturated aliphatic olefin having from 2 to 20 carbon atoms.*

*37. The process as defined by claim 36, the olefin comprising a monoethylenically unsaturated compound having a terminal or internal double bond.*

* * * * *